United States Patent [19]

Kasche et al.

[11] Patent Number: 5,326,698
[45] Date of Patent: Jul. 5, 1994

[54] METHOD OF PURIFICATION OF PENICILLIN AMIDASE USING PHENYLBUTYLAMINE-EUPERGIT

[75] Inventors: Volker Kasche, Bremen; Fridolin Löffler, Bensheim; Dieter Krämer, Mainz; Gerd Janowski, Münster, all of Fed. Rep. of Germany

[73] Assignee: Roehm GmbH Chemische Fabrik, Darmstadt, Fed. Rep. of Germany

[21] Appl. No.: 960,264

[22] Filed: Oct. 13, 1992

Related U.S. Application Data

[63] Continuation of Ser. No. 489,539, Mar. 7, 1990, abandoned.

[30] Foreign Application Priority Data

Mar. 18, 1989 [DE] Fed. Rep. of Germany ....... 3909018

[51] Int. Cl.$^5$ .......................... C12N 9/86; C12N 9/00
[52] U.S. Cl. ..................................... 435/231; 435/183
[58] Field of Search ........................... 435/183, 231

[56] References Cited

U.S. PATENT DOCUMENTS

| | | | |
|---|---|---|---|
| 4,006,059 | 2/1977 | Butler | 195/68 |
| 4,208,309 | 6/1980 | Kraemer et al. | 260/8 |
| 4,511,694 | 4/1985 | Kraemer et al. | 525/54.1 |

FOREIGN PATENT DOCUMENTS

| | | |
|---|---|---|
| 190556B | 12/1981 | Czechoslovakia . |
| 2722751 | 9/1982 | Fed. Rep. of Germany . |
| 155051A | 12/1984 | India . |
| 01296987 | 11/1989 | Japan . |

OTHER PUBLICATIONS

Josic, D. J., Die Angewandte Makromolekulare Chemie 166/167:249–256 (1989).
Dunn, B. M. et al, Arch Biochem Biophys 198:533–540 (1989).
Kasche et al., J. Chrom., 510:149–154 (1990).
Stevenson et al., Can. J. Biochem, 49:119–26 (1971).
Fei et al, Shengwu Huaxue Yu Shengwu Wuli Xuebao 21:315–21 (1989) (abstract).
Dhal PK et al, J. Polymer Sci: Poly Chem 23:319–25 (1985).
Sudhakaran UK et al, Biotecnol Lett 9:539–42 (1987).
Biochemistry vol. 17, No. 13, Jun. 27, 1978, pp. 2484–2489, Washington, D.C., US; R. T. Dworschack et al.: "Interaction of Kidney Renin with Aryl-, Isoalkyl-, and N-Alkyl-Substituted Sepharose Derivatives: Multipliety of Interaction Sites".
Bissoli et al, Regional Levels of Cholinergic, Gabaergic and Excitatory Amino Acidic Transmitters in Fish Telencephalon, *Comp. Biochem. Physiol.*, vol. 93C, No. 2, pp. 317–320 (1989).
Ukr. Biokhim. Zh., vol. 55, No. 5, pp. 577–591 (1983) (with English-language Summary).

*Primary Examiner*—Douglas W. Robinson
*Assistant Examiner*—S. Sancier
*Attorney, Agent, or Firm*—Oblon, Spivak, McClelland, Maier & Neustadt

[57] ABSTRACT

An enzyme is purified by absorbing enzymes in an aqueous solution on a specific carrier material T-PbA to which is covalently bound phenyl butylamine ligand groups.

10 Claims, No Drawings

METHOD OF PURIFICATION OF PENICILLIN AMIDASE USING PHENYLBUTYLAMINE-EUPERGIT

This application is a continuation of application Ser. No. 07/489,539, filed on Mar. 7, 1990, now abandoned.

BACKGROUND OF THE INVENTION

1. Field of the Invention

The present invention relates to a method for purifying a protein, particularly enzymes from biomass, particularly the enzyme penicillin amidase.

2. Description of the Background

It is known that proteins, particularly enzymes, can be purified by way of hydrophobic chromatography. For example, the enzyme penicillin amidase (penicillin acylase PcA) can be purified from *E. coli* (E.C. 3.5.1.11), which is used for technical conversion of fermentatively produced penicillins in 6-amino penicillin acid (df. H. J. Rehm & G. Reed in Biotechnology, Vol. 7a, p. 168, 169 VCH 1987), on phenyl glycine sepharose, by means of affinity chromatography (Indian Patent 15 50 51A, Purification of Penicillin Acylase Enzyme, P. S. Borkar and P. B. Majahan). Furthermore, benzyl EUPERGIT is used for purification of PCA by affinity chromatography. Affinity chromatography with affinity ligands consisting of phenylacetic acid or its derivatives is described in Chem. Abstracts 97, 35363a. Other methodology employs conjugates of agarose or sepharose with ampicillin or amoxicillin as matrices for affinity chromatography (Indian Patent 155 050; P.B. Mahajan et al., Hind. Antibiot. Bull. 24 (1-2) 38, 1982, Chem. Abstracts97, 87551e as well as Chem. Abstracts95, 110 740 K).

The methods which have been proposed thus far are complicated, without exception, both with regard to the number of individual operations required and with regard to the apparatus necessary to perform the operations. In fact the significant time required for protein purification is unsatisfactory. A need therefore continues to exist for a simplified method of protein and purification isolation which is fast and involves minimal loss of protein.

SUMMARY OF THE INVENTION

Accordingly, one object of the present invention is to provide a method of purifying enzymes which minimizes loss of enzyme.

Briefly, this object and other objects of the present invention as hereinafter will become more readily apparent can be attained in a method of purifying an enzyme on a substrate which contains aromatic groups by absorbing enzymes in an aqueous solution on a specific carrier material T-PbA to which is covalently bound phenyl butylamine ligand groups.

DETAILED DESCRIPTION OF THE EMBODIMENTS

The present invention is a method for purifying enzymes which involves substrates which contain aromatic groups, especially phenyl groups. The invention especially is directed to the purification of the enzyme penicillin amidase (PcA) (cf. E.C.3.5.1.11), especially the enzyme from *E.coli* or from *B. megaterium*. In the method of the invention, the protein to be purified is fixed to a specific carrier T, containing phenyl butylamine, which has been covalently bonded to the carrier by reaction with an active group AG of the carrier, by means of hydrophobic absorption.

Suitable carrier materials include those of natural or synthetic origin. The active groups AG of the carrier material are believed to react with phenyl butylamine by way of a nonionic bonding mechanism. Therefore, no change in the electrochemical character of the ligand, phenyl butylamine, should occur. This requirement is fulfilled, for example, in an especially advantageous way, with a copolymerizate which consists of the matrix component (meth) acrylamide, a cross-linker, e.g. N,N-methylene-bis-(meth)acrylamide and the bonding-active component glycidyl (meth)acrylate and/or allyl glycidyl ether. Products are commercially available under the trademark EUPERGIT C ®(Rohm GmbH). Furthermore, other carrier materials are also suitable, for example cross-linked agarose which is substituted with epoxide groups ("epoxy activated SEPHAROSE ®"), as well as synthetic polymer carriers based on cross-linked polyvinyl acetate, whose acetyl groups have been removed by hydrolysis and substituted with epoxy groups. (VA-epoxy carrier from Riedel-de Haen). Suitable carriers T-PbA are also obtained if the carrier materials mentioned above are substituted with tresyl groups (K. Nilsson and K. Mosbach, Biochem. Biophys. Res. Communications, Vol. 102, No. 1, pp. 449-457, 1981), as active groups AG, instead of the epoxy groups (e.g. "tresyl activated Sepharose ®" or tresyl-activated EUPERGIT ® Diol).

Any known process can be employed to produce the carrier material T-PbA which is to be used for protein purification. (The carrier pre-stages are designated as T-VS, while their activated form is abbreviated as T-VS-A.) The bonding-active component AG can be introduced either by polymer-analog conversion, e.g. by addition of epichlorhydrin at hydroxyl groups of the polymer, or by direct copolymerization of monomers which contain these bonding-active groups.

The most suitable matrix monomers MM are nonionic hydrophilic vinyl compounds such as (meth)acrylamide, where the amide group can be substituted with (hydroxyl-substituted) $C_1$-$C_4$ alkyl groups, if necessary, furthermore hydroxyalkyl esters with $C_1$-$C_6$ alkyl groups in the ester portion of (meth)acrylic acid, e.g. esters of polyols, furthermore vinyl alcohols, allyl alcohol, vinyl esters such as vinyl acetate and vinyl propionate. The proportion of the monomer containing the bonding-active component AG in the carrier material amounts to 4 to 40% by weight, as a rule. The proportion of the cross-linking monomer component is generally between 5-80% by weight. The proportion of the matrix monomer constitutes the remainder up to a total of 100% by weight.

Suitable cross-linking monomers are known cross-linkers, preferably nonionic, hydrophilically cross-linking monomers such as N,N'-methylene-bis-(meth)acrylamide, polyols esterified several times, but at least twice, with (meth)acrylic acid, especially pentaerythritol (meth)acrylic acid esters of this type.

The ligand density is most practically 10-2,000 umol PbA groups per gram carrier material in the dry state, preferably 50-500 μmol.

In connection with the present invention, carrier material with a macroporous structure, preferably of spherical shape, to which phenyl butylamine is covalently bonded, are of particular interest (cf. Jahrbuch der Biotechnology {Yearbook of Biotechnology}, 1986-1987, p. 404, Carl-Hanser-Verlag). Such macroporous structures are demonstrated, for example, by the commercially available products of the EUPERGIT C® type (EUPERGIT c, Eupergit C30N, EUPERGIT C250 L), also by FRACTOGEL® or TOIOPEARL®, as well as corresponding macroporous ion exchangers (e.g. LEWATITE® from Bayer AG, AMBERLITE from ROhm & Haas), after corresponding conversion to nonionic materials. As already explained, the (activated) carrier material pre-stages T-VS-A of the EUPERGIT C® type ar of particular interest. This material is a cross-linked copolymerizate of acrylamide or methacrylamide and glycidyl acrylate or methacrylate, which preferably consists of bead-shaped particles. Such matrix polymerizates are described in DE-C 27 22 751, i.e. U.S. application Ser. No. 4,190,713, as well as U.S. application Ser. No. 4,511,694. The beads generally possess a diameter of 5–1,000 μm, especially 30–1,000 μm. The content of glycidyl groups in the carrier material normally range from 0.8 –2.5 umol per mg dry carrier material. Other characteristics of the carrier material are as follows:

| Characteristic | Dimension |
| --- | --- |
| average grain size: | 140–180 μm |
| pore diameter: | 40 nm |
| exclusion limit = $M_{lim}$: | $2 \times 10^5$ Daltons |
| binding-active surface: | 180 m$^2$/g (dry) |
| epoxide content: | 800–1000 mmol/g (dry) |
| water absorption: | 2.3 ml/g (dry) |
| density = $d_4 20$: | 1.20 |
| bulk density: | 0.34 g/ml |
| binding capacity: (under usual conditions) | |
| human albumin: | 48 mg/g (moist) |
| human IgG: | 34 mg/g (moist) |
| swelling behavior with regard to water: | 1:1.4<br>1 ml (dry) yields 1.4 ml (moist) |
| solubility (in water, buffers or organic solvents): | insoluble |
| pressure stability: | 300 bar |

The macroporous structure of the beads with channels and cavities, having a diameter of 0.1–2.5 μm (1,000 to 25,000 Å) can be observed under the electron microscope. At these sizes the enzyme or substrate molecules with a size of 10–100 Å can reach the entire interior of the macroporous matrix.

The liquid responsible for protein purification is generally produced by reaction of the carrier material pre-stage T-VS-A with the amine phenyl butylamine. In general, the reaction can be carried out by direct reaction, for example, of the carrier material containing epoxide groups, with phenyl butylamine, preferably in a suitable liquid medium, e.g. water or an alcohol such as ethanol. For practical purpose the amine is used in a certain excess relative to the functional groups of the T-VS-A. The conversion is preferably carried out at elevated temperature, e.g. in the range of 30° to 100° C. After the reaction, the excess amine is removed by acid treatment, for example with dilute sulfuric acid, and washing with water.

In detail, bonding of the phenyl butylamine to the carrier material pre-stage T-VS-A can be carried out in the following manner. In a suitable inert liquid medium, such as ethanol, for example, or a ketone such as acetone, the carrier material, pre-stage T-VS-A, is mixed with phenyl butylamine, preferably in excess relative to the number of bonding-active groups AG of the pre-stage material, e.g. an excess up to five times, preferably about twice, for practical purposes and allowed to react over a certain period of time, as a function of the temperature selected, which can lie between room temperature and approximately 100° C., for example, at the boiling temperature of the medium, generally between 3 and 72 hours. Subsequently, the product is washed with the solvent and then with water to remove the excess amine, with the organic medium comprising 5–15 times and the water comprising 10–30 times the weight of the dry carrier material. Subsequently, washing is still carried out with a dilute mineral acid, especially with 0.5M sulfuric acid in an amount of 3–5 times the weight of the dry carrier material and if necessary, refluxing for 10–30 minutes in 0.5M sulfuric acid (3 times weight amount) is carried out, followed by washing with water until a neutral reaction is obtained.

The reaction of the carrier material T-PbA which can be used with the protein, especially the enzyme, in particular the enzyme of the penicillin amidase type, can be generally carried out as follows. The homogenate from enzyme production is preferably sedimented in a cooling centrifuge, for example at 5,000 to 10,000 g, then the clear top fraction, which generally contains 15–20 units penicillin amidase per ml, is placed into a chromatography column charged with the carrier material T-PbA, which was filled with a buffer solution Buffer A, for example, 0.05 molar potassium phosphate buffer pH 7.5 plus 1 mol NaCl. A column charged in this way can be charged with 30–100 units penicillin amidase per milliliter moist carrier, so that there are 10 to 80 mg protein per milliliter carrier. The columns have a diameter in the range of 1 mm to 30 cm and a height of approximately 10 cm to 1 m and more. It is recommended that a flow rate (linear flow) of 60–100 cm/hour be maintained. The column is rinsed with Buffer A and the enzyme is then eluted with an elution buffer, 0.1 mol sodium formate buffer at pH 3.8 in the case of penicillin amidase, and then collected in 0.1 volume of a 1 molar potassium phosphate buffer pH 7.5. In general, the elution process is concluded in 5 to 60 minutes, preferably approximately 20±10 min, depending on the column. The eluate is suitable, for example, directly for immobilization, especially covalent immobilization on a solid carrier, e.g. on EUPERGIT C. The immobilization yield is approximately 80%, product activity 100 units/g moist weight.

The same column can be used for enzyme purification at least 50 times in a row, as long as the column was treated with 2–5 column volumes of a protease solution, preferably with 0.006 Anson units at pH 10, after every run. Suitable proteases include alkaline proteases, especially those of bacterial origin. (Cf. Keay, Process Biochemistry, 17–21, 1971; H. J. Rehm, G. Reed, Biotechnology, Vol. 7a, loc. cit. p. 156–168; Ullmann's Encyclopadie der Techn. Chemie {Encyclopedia of Technical Chemistry}, 4th edition, Vol. 10, 517–522, Verlag Chemie, 1975). Specifically, alkaline proteases include those from *Bacillus subtilis*, from *Aspergillus sp.*, especially *A. oryzae*. The proteolytic activity of the enzymes is most practically determined by the so-called Löhlein-Volhard method ("the Löhlein-Volhard method for determination of proteolytic activity," Gerbereitechnisches Taschenbuch [Handbook of Tanning Technology], Dresden-Leipzig, 1955), the units of which are abbreviated as "LVE" ((Löhlein-Volhard units). An LVE unit is understood to be that amount of enzyme which digests 1.725 mg casein under the specific conditions of the method. For the determination of activity of enzymes which are active in the acid range, which is derived from the Anson method (M. L. Anson, J. Gen. Physiol. 22, 79 (1939)), the following applies: The units are designated as "proteinase units (hemoglobin)"" = $U_{Hb}$. One $U_{Hb}$ corresponds to that amount of enzyme which catalyzes the release of fragments of hemoglobin soluble in trichloracetic acid equivalent to 1 mol tyrosine per minute at 37° C. (measured at 280 nm). $1mU_{Hb} = 10^{-3}U_{Hb}$.

The advantageous effects of the present invention in comparison to the methodology of the prior art is the extraordinarily high bonding capacity of the present carrier material. This also results in the possibility of immobilizing the protein directly on the carrier, by cross-linking, which makes it possible to obtain a product with satisfactory activity, e.g. for industrial use.

Another advantage consists of the possibility of carrying enzyme purification out quickly. The time saved in comparison to the art known methods amounts to a factor of 2 to 5. In addition there is the advantage that a relatively small volume is required for elution.

As an alternative to isolation of the enzymes, the enzyme absorbed on the carrier material can also be used directly as an immobilized enzyme, after appropriate cross-linking. (Cf. Ullmann's Encyclopadie der Techn. Chemie, 4th edition, Vol. 10, p. 542, Verlag Chemie, 1975).

The proteins produced on an industrial scale, especially the enzymes, are generally obtained from biomass. The literature gives sufficient information about the production of biomass from which the enzyme penicillin amidase (3.5.1.11) can be obtained (e.g. H. J. Rehm & G. Reed in Biotechnology, Vol. 7a, VCH 1987; Ullmann's Encyclopedia of Industrial Chemistry, 5th edition, Vol. A9, p. 371-382; VCH 1987). For further processing, homogenization of the biomass must be carried out, for example according to the French Press method using a French Pressure Cell Press (SLM-Aminco) or using the high-pressure dispersion apparatus of Manton-Gaulin (cf. Ullmann's Encyclopadie der Techn. Chemie, 4th edition, Vol. 10, loc, cit., p. 493 –495). Subsequent to homogenization, separation of the enzyme solution takes place by means of centrifugation or filtration, as already described above.

Having now generally described this invention, a further understanding can be obtained by reference to certain specific examples which are provided herein for purposes of illustration only and are not intended to be limiting unless otherwise specified.

EXAMPLE 1

Production of EUPERGIT C® substituted with phenyl butylamine (PbA-EUPERGIT).

In a 4 l three-necked flask, 50 ml 98% phenyl butylamine is dissolved in 1325 ml absolute ethanol and 250 g dry EUPERGIT C are added while stirring the solution (saber stirred). The suspension is boiled for 4 hours while the solution is refluxed with light stirring. Subsequently, the cooled material is transferred to a frit G1 and washed with approximately 3 l technical ethanol and approximately 7 l millipore filtered water in small amounts (550 ml). After thorough suction filtration, the material is slurried once with 0.5M sulfuric acid (allow to act), suction filtered again and transferred back to the reaction flask with 750 ml 0.5M sulfuric acid. This suspension is boiled under reflux for 30 min. Subsequently, the material is washed free of acid on a G1 frit using millipore filtered water (approximately 10 l). The material is heat-sterilized at 121° C. for 30 min.

EXAMPLE 2

Purification of penicillin amidase from *E. coli* using affinity chromatography. Column material: EUPERGIT C® substituted with phenyl butylamine (PbA EUPERGIT C) in accordance with Example 3.

To a column (volume: 8 ml; diameter: 1 cm) in Buffer A (0.05M potassium phosphate buffer, pH 7.5 plus 1M NaCl), 15 ml top fraction of the *E. coli* homogenate (10.7 mg/ml protein, 39 U/l moist carrier activity) was applied at a 1 ml/min (76.4 cm/hour linear flow), washed with 30 ml Buffer A and the enzyme was eluted in 35 ml with Buffer B (0.1M sodium formate buffer pH 3.8). The yield of enzyme is 89%. The specific activity of the enzyme increases from 2.0 U/mg in the top fraction of the homogenate to 10.2 U/mg in the eluate. In order to expose the enzyme to the acidic elution buffer for only a short time, 1 ml potassium phosphate buffer is added to the fractions (5 ml each) of the eluate. Subsequently, the column is regenerated with 40 ml of a solution of 0.006 Anson Units of bacterial alkaline protease in 0.02M glycine NaOH buffer, pH 10, and washed neutral with 60 ml Buffer A, before a new cycle begins.

EXAMPLE 3

Immobilization of Penicillin Amidase on EUPERGIT C

The penicillin amidase (PcA) purified via a PBA-Eupergit column was dialyzed against water and concentrated by means of a rotary evaporator. Since the PcA was very cloudy, it was centrifuged for 15 minutes at 20,000 rpm and 4° C. The top fraction was clear afterwards.

Activity Measurement

The PcA is diluted 1:10 with 0.1M potassium phosphate buffer (pH 7.5) (at approximately 180 U/ml). The enzymatic activity was determined against penicillin-G-potassium (crude) as the substrate, by alkalimetric titration at pH 7.8. For this, 20 ml of a 2% substrate solution in 0.05M potassium phosphate buffer (pH 7.8) were used each time, and the titration was carried out at 37° C. with 0.5M NaOH.

Immobilization

510 U PcA placed in 1.5M potassium phosphate buffer and are brought to 4 ml total volume. The resulting batch is placed onto 1 g Eupergit C. The mixture is then allowed to stand 23° C. for 72 hours. Then the batch is washed 3 times with 0.1M potassium phosphate buffer pH 7.5, on a frit.

Moist yield: 3.49 g
Activity: 91 U/g

EXAMPLE 4

Activity Measurement of Immobilized Penicillin Amidase

Principle

The method is based on the titration of phenylacetic acid which is released and occurs during enzymatic hydrolysis of penicillin-G-potassium at pH 7.8° and 37° C.

Apparatus recording pH-stat. autotitration system, from Radiometer-Copenhagen A/S or Metrohm SA (Switzerland)
automatic burette
pH meter
titration stand
servograph
reaction vessel (100 ml volume) with tempered outside mantle and a stirrer device (no magnetic stirrer; destroys the beads).
thermostat.

Method

A 500 mg amount of EUPERGIT-PcA is placed into a reaction vessel heated to 37° C., after having been washed several times with deionized water. 20 ml substrate solution, heated to 37° C., are placed on the enzyme carrier (substrate: 2% penicillin-G-potassium or sodium (crude) are dissolved in 0.05M potassium phosphate buffer of pH 7.5 and 0.05% hydroxybenzoic acid ethyl ester is added to the solution). While stirring constantly, 0.5M NaOH is added through an automatic burrette, controlled by a pH stat at pH 7.8. At the same time, NaOH consumption is recorded against the reaction time (first determination). The incubation is stopped after 10 minutes, the enzyme carrier is placed onto a glass frit (P2 or P3) and suction filtered, and is washed 3 times with 2 ml 0.1M potassium phosphate buffer pH 7.5. The washed beads are placed back into the reaction vessel and the activity determination (second determination) is carried out as described above. The activity determination is repeated once again with the sample obtained in this way (third determination).

Calculation of the Activity of the Immobilized Catalyst

The activity of the enzyme carrier is indicated in U/g moist product. A unit is defined as $\mu$mol hydrolyzed penicillin-G per minute (U=$\mu$mol/min). A 1 ml amount of 0.5M NaOH corresponds to 500 umol hydrolyzed penicillin-G. For the determination of activity, the linear progression of the curve is used (usually the section between the 1 and 5 minute). Activity of the immobilized catalyst results from the average value for activity of the second and third incubation.

EXAMPLE 5

Immobilization of the enzyme penicillin amidase from PBA-Eupergit by cross-linking. A 10 g amount of PBA-Eupergit (moist weight) is washed three times in 10 volumes 1M phosphate buffer, pH 7.5, each time, and suction filtered on a glass frit. The moist material obtained is placed into a beaker with 20 mol of an *E. coli* homogenate according to Example 6, with a penicillin amidase activity of 39 u/ml, and shaken at 21° C. for 60 minutes. The product is then separated by filtration (glass frit/vacuum), washed twice with 1.0M potassium phosphate buffer (pH 7.5) and subsequently suspended in 10 ml of 1.0M potassium phosphate buffer. Then 0.250 ml of a 25% aqueous glutardialdehyde solution are added the solution being stabilized with ion exchange resin Amberlite A 21R. The suspension is shaken for 2 hours, then washed three times with 0.05M potassium phosphate buffer (pH 7.5). Moist yield 9.8 g. The activity determination yielded 62% activity yield and product with 49 U/g moist weight.

EXAMPLE 6

Obtaining Raw Extract Form *Escherichia Coli* Cells

A 20 l amount of a fermented culture solution was centrifuged at 4° C. for 20 minutes (10,000 g, Cryofuge, Heraeus). After decanting of the top fraction, the moist cell mass was suspended in 900 ml 0.05M potassium phosphate buffer pH 7.5 and centrifuged again. After the washing process, the moist cell mass (550 g) was again suspended in 1,200 ml 0.05M potassium phosphate buffer pH 7.5. The cell suspension was frozen at $-80°$ C. before cell digestion. The *E. coli* cells have an activity of 58 U/g cells against 2% penicillin-G solution (20 ml, 37° C). Cell digestion took place according to the French Press method (1,000 bar pressure difference, French Pressure Cell Press, SLM-Aminco). In order to avoid activity losses, the suspension was thawed in ice water right before cell digestion. Aliquots of 40 ml cell suspension were each homogenized four times, in order to obtain maximum activity of the homogenate. After four subsequent cycles, an activity of the homogenate against a 2% penicillin-G solution (20 ml, 37° C.) of 23 U/ml was obtained. The homogenate was frozen directly after cell digestion, at $-80°$ C. To separate the cell fragments, the thawed homogenate was centrifuged at 4° C. for 30 minutes (10,000 g, Cryofuge, Heraeus). The top fraction can be used directly for subsequent chromatographic isolation of penicillin amidase (activity of the top fraction 18.75 U/ml).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method for purification of penicillin amidase on substrates which contain aromatic groups, comprising:
   absorbing pencillin amidase in a buffered aqueous solution at a pH near neutral on a specific carrier material T-PbA by hydrophobic interaction, said carrier material prepared by covalently bonding phenylbutylamine to a carrier pre-stage T-Vs-A by reaction of the phenylbutylamine with glycidyl groups on the carrier, which glycidyl groups constitute the activated group on the carrier substrate; and
   eluting the absorbed enzyme from the carrier substrate with a buffered aqueous acid eluting solution.

2. The method of claim 1, wherein the eluting aqueous solution has a pH of about 3.8.

3. The method according to claim 1, wherein the activated carrier pre-stage T-Vs-A is a cross-linked copolymerizate formed from the matrix monomers acrylamide, methacrylamide, the bonding-active monomers glycidyl acrylate, glycidyl methacrylate, and the cross-linking monomers N,N'-methylene-bis-acrylamide and N,N'-methylene-bis-methacrylamide.

4. The method according to claim 3, wherein the proportion of bonding-active monomers in the carrier pre-stage T-Vs-A is 4 to 40% by weight.

5. The method according to claim 3 or 4, wherein the proportion of cross-linking monomers in the carrier pre-stage T-Vs-A is 5 to 80% by weight.

6. The method according to claim 1, wherein the ligand density of the fixed phenyl butylamine is 10 to 2,000 umol per gram of carrier material.

7. The method according to claim 1, wherein the enzyme penicillin amidase (E.C. 3.5.1.11) is purified.

8. The method according to claim 1, wherein the enzyme, absorbed on carrier material T-PbA is eluted by means of a slightly acidic buffer solution and the eluate is adjusted to a pH close to the neutral point again.

9. The method according to claim 8, wherein the carrier material T-PbA is treated with a protease after elution of the enzymes, and subsequently washed.

10. The method according to claim 9, wherein the enzyme is an alkaline protease in an alkaline buffer and subsequent to absorption the carrier material T-PbA is washed with a buffer in the neutral range.

* * * * *